United States Patent [19]

Pallos et al.

[11] 3,978,219

[45] Aug. 31, 1976

[54] NICOTINAMIDOXIME AS AN ANTI-INFLAMMATORY AGENT

[75] Inventors: Ferenc M. Pallos, Walnut Creek; Jack R. DeBaun, Sunnyvale, both of Calif.

[73] Assignee: Stauffer Chemical Company, Westport, Conn.

[22] Filed: July 25, 1975

[21] Appl. No.: 599,274

[52] U.S. Cl. .................................. 424/264; 424/266
[51] Int. Cl.² .............. A61K 31/455; A61K 31/465
[58] Field of Search ................... 424/264, 327, 266

[56] References Cited

UNITED STATES PATENTS

| | | | |
|---|---|---|---|
| 2,668,115 | 2/1954 | Wolf | 424/327 |
| 3,781,444 | 12/1973 | Ezzell et al. | 424/327 |
| 3,829,581 | 8/1974 | Ellis | 424/327 |

*Primary Examiner*—Stanley J. Friedman
*Attorney, Agent, or Firm*—Edwin H. Baker

[57] ABSTRACT

Nicotinamidoxime as an anti-inflammatory agent.

1 Claim, No Drawings

NICOTINAMIDOXIME AS AN ANTI-INFLAMMATORY AGENT

This invention relates to nicotinamidoxime which is useful as an anti-inflammatory agent.

The compound, nicotinamidoxime, has the following structural formula

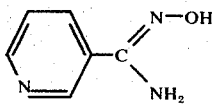

Nicotinamidoxime will hereinafter be called Compound Number 1.

Anti-Inflammatory Screening

The compound of the present invention has pharmaceutical activity especially as an anti-inflammatory agent. Anti-inflammatory activity is demonstrated by a test which involves the diminution of experimental edema induced in the hind paw of a rat by the injection of carrageenin.

Carrageenin injected into the paw of the rat produces an edematous condition which simulates part of the inflammatory process. Non-steroidal anti-inflammatory compounds inhibit the formation of this edema.

Methods and Procedures

The procedure used for measuring the inhibition of carrageenin-induced edema is a standard procedure well known in the pharmaceutical art and is as follows:

Male rats (Long Evans Strain) weighing between 130–200 grams are used in this assay. Five rats each are used in the treatment groups and in the known standard control; whereas ten rats are used in the control edema group. Unless otherwise indicated, phenylbutazone is administered orally at 100 mg/kg to the standard control group. The edema control group is administered the vehicle which consists of 0.25% methylcellulose solution. All of the rats are fasted for at least 15 hours prior to the test. Water is available ad libitum. All of the experimental drugs are given orally and dissolved or suspended in 0.25% methylcellulose solution. One hour after administration of the test compound, 0.05 ml of a 1% sterile solution of carrageenin is injected into the plantar tissues of the left hind paw of each rat. Three hours after carrageenin administration, the paw volumes of injected paws are then measured by means of a water displacement apparatus. The apparatus used is a modification of that described by Adamkiewicz et al., Canadian Journal of Biochemistry and Physiology, 33: 332, 1955. The amount of edema is calculated and the percent reduction of edema from control values is determined. The mean volume of edema, based on 50 determinations, is 1.25 cc with a standard deviation of 0.226 cc. A reduction in edema greater than 25% of the control value is considered significant. Based on 46 determinations, phenylbutazone produced a mean inhibition of edema of 43.8% with a standard deviation of 13.4%.

We have found that the compound of this invention produces a significant inhibition of induced edema in rats at a dose rate of 200 mg/kg.

Table I shows the reduction in edema in the hind paw of the rat according to the above-described test procedure, at 200 mg/kg unless otherwise indicated.

TABLE I

| Compound Number | Percent Reduction in Edema at 200 mg/kg Percent Reduction of Induced Edema |
|---|---|
| 1 | 65 |

The compound of the present invention, either alone or in the form of pharmaceutical composition may be administered to an animal subject in any of a number of forms and via any of several routes. Thus, the compound or composition thereof may be orally administered in the form of tablets, pills, capsules, or in the form of a suspension. The compound may also be administered parenterally in the form of an injectable solution or suspension. The compound or composition thereof may also be administered topically, in the form of an ointment or rectally, in the form of a suppository.

When orally administering the compound or composition, use can be made of a tablet, pill or capsule consisting entirely of the desired compound, although ordinarily, a composition comprising an effective amount of the compound and varying amounts of one or more physiologically inert materials such as carriers, vehicles, binders and the like will be used. Additionally, the compound may be orally administered in the form of a suspension thereof in a suitable vehicle such as a syrup.

When parenterally administering the compound or composition, use may be made of a parenteral solution or suspension of the compound in a suitable solvent or suspension medium.

The compound of the present invention may also be administered rectally in the form of a suppository comprising an effective amount of the desired compound and a suitable vehicle such as petroleum jelly.

Finally, the compound of the present invention may be applied topically in the form of an ointment, salve, cream or lotion comprising an effective amount of the desired compound and a suitable vehicle such as petroleum jelly, etc.

We claim:

1. A method of treatment of an inflammatory condition in a mammal comprising administering to said mammal a therapeutically effective amount of nicotinamidoxime.

* * * * *